US011759625B2

(12) United States Patent
Ito et al.

(10) Patent No.: US 11,759,625 B2
(45) Date of Patent: Sep. 19, 2023

(54) ELECTRICAL TREATMENT DEVICE

(71) Applicant: OMRON HEALTHCARE Co., Ltd., Kyoto (JP)

(72) Inventors: Tamaki Ito, Kyoto (JP); Tsuyoshi Ogihara, Kyoto (JP); Taiki Yukutake, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/886,931

(22) Filed: May 29, 2020

(65) Prior Publication Data

US 2020/0289813 A1    Sep. 17, 2020

Related U.S. Application Data

(63) Continuation of application No. PCT/JP2018/043400, filed on Nov. 26, 2018.

(30) Foreign Application Priority Data

Dec. 14, 2017  (JP) .................................. 2017-239616

(51) Int. Cl.
*A61N 1/04* (2006.01)
*A61N 1/24* (2006.01)

(52) U.S. Cl.
CPC ......... *A61N 1/0452* (2013.01); *A61N 1/0484* (2013.01); *A61N 1/24* (2013.01)

(58) Field of Classification Search
CPC ...... A61N 1/0452; A61N 1/0484; A61N 1/24; A61N 1/36014; A61N 1/321; A61N 1/0472; A61N 1/0456
See application file for complete search history.

(56) References Cited

U.S. PATENT DOCUMENTS 6,272,383 B1    8/2001  Grey et al.
6,535,760 B1    3/2003  Grey et al.
(Continued)

FOREIGN PATENT DOCUMENTS

JP    2006-525062 A    11/2006
JP    2016-533254 A    10/2016
WO    2009/095801 A1    8/2009

OTHER PUBLICATIONS

International Search Report of the International Searching Authority for PCT/JP2018/043400 dated Feb. 19, 2019.
(Continued)

*Primary Examiner* — Ankit D Tejani
*Assistant Examiner* — Joshua Brendon Solomon
(74) *Attorney, Agent, or Firm* — Birch, Stewart, Kolasch & Birch, LLP

(57) ABSTRACT

A electrical treatment device (100) includes a band-like member (20), a first electrode portion (41), a second electrode portion (42), a first mark portion (31) configured to be aligned with a specific position of a right lower limb when the band-like member (20) is wrapped around the right lower limb such that the first electrode portion (41) is guided to a first target position and the second electrode portion (42) is guided to a second target position, and a second mark portion (32) configured to be aligned with a specific position of a left lower limb when the band-like member (20) is wrapped around the left lower limb such that the first electrode portion (41) is guided to a third target position and the second electrode portion (42) is guided to a fourth target position.

11 Claims, 7 Drawing Sheets

(56) References Cited

U.S. PATENT DOCUMENTS

| | | |
|---|---|---|
| 9,827,418 B2 | 11/2017 | Southwell et al. |
| 9,962,544 B2 | 5/2018 | Southwell et al. |
| 10,279,174 B2 | 5/2019 | Southwell et al. |
| 10,279,175 B2 | 5/2019 | Southwell et al. |
| 2003/0187483 A1 | 10/2003 | Grey et al. |
| 2003/0199943 A1* | 10/2003 | Katz .................... A61N 1/0408 607/48 |
| 2007/0106343 A1 | 5/2007 | Monogue et al. |
| 2010/0312307 A1 | 12/2010 | Minogue |
| 2013/0085317 A1* | 4/2013 | Feinstein ........... A61N 1/37247 600/14 |
| 2013/0158627 A1* | 6/2013 | Gozani ................ A61N 1/0456 607/46 |
| 2016/0235981 A1 | 8/2016 | Southwell et al. |
| 2016/0250463 A1 | 9/2016 | Southwell et al. |
| 2018/0133468 A1 | 5/2018 | Southwell et al. |
| 2018/0289955 A1 | 10/2018 | Southwell et al. |

OTHER PUBLICATIONS

English translation of International Search Report of the International Searching Authority for PCT/JP2018/043400 dated Feb. 19, 2019.

Chinese Office Action and Search Report for Chinese Application No. 201880073098.X, dated Mar. 10, 2023, with an English translation.

\* cited by examiner

ELECTRICAL TREATMENT DEVICE

CROSS-REFERENCE TO RELATED APPLICATIONS

This is a continuation of International Application 2017-239616, with an international filing date of Dec. 14, 2017, and PCT/JP2018/043400 with an international filing date of Nov. 26, 2018, and filed by applicant, the disclosure of which is hereby incorporated by reference in its entirety.

TECHNICAL FIELD

The present disclosure relates to an electrical treatment device.

BACKGROUND ART

There have been known electrical treatment devices configured to relieve stiffness and pain. Such an electrical treatment device provides stimulation by outputting an electrical signal to a muscle via the electrode portion with an electrode portion in contact with a surface of a body, such as an abdomen or a back.

For example, JP 2016-533254 T (Patent Document 1) provides an electrical stimulation device configured to apply electrical stimulation to the body mainly for the purpose of treating a waste evacuation dysfunction. In this electrical stimulation device, a belt including a first portion configured to cover a waist from a back side and a second portion configured to cover a front lower abdomen from a front side is wrapped around the waist of a user. A plurality of electrode portions are provided to the first portion and the second portion so as to come into contact with a body surface of the user. Further, an alignment pad is provided to the first portion. By laying the alignment pad on a spine, it is possible to bring the plurality of electrode portions into contact with appropriate locations on the body surface.

CITATION LIST

Patent Literature

Patent Document 1: JP 2016-533254 T

SUMMARY OF INVENTION

Technical Problem

Although the electrical stimulation device described in Patent Document 1 is configured to be wrapped around a lower portion of a torso, the user may want to wrap the electrical stimulation device around a left lower limb or a right lower limb rather than the torso depending on treatment sites. Positions of the left lower limb and the right lower limb preferably electrically stimulated are different and thus, when one electrical stimulation device is used for both the left lower limb and the right lower limb without any measures, it is difficult to bring the electrode portions into contact with the appropriate locations on the body surface. On the other hand, when an electrical stimulation device for the left lower limb and an electrical stimulation device for the right lower limb are each manufactured, manufacturing costs increase.

The present disclosure has been made in view of problems such as described above, and an object of the present disclosure is to provide an electrical treatment device capable of bringing an electrode portion into contact with an appropriate location on a body surface, even when used for both a left lower limb and a right lower limb.

Solution to Problem

An electrical treatment device according to the present disclosure includes a band-like member configured to be wrappable around both a right lower limb and a left lower limb of a user, a first electrode portion and a second electrode portion supported by the band-like member such that the first electrode portion and the second electrode portion come into contact with a body surface of the user in a wrapped state obtained by wrapping the band-like member around the right lower limb or the left lower limb, and configured to deliver a current to the user, a first mark portion configured to be aligned with a specific position of the right lower limb in a case where the band-like member is wrapped around the right lower limb such that the first electrode portion is guided to a first target position of the right lower limb and the second electrode portion is guided to a second target position of the right lower limb, and a second mark portion configured to be aligned with a specific position of the left lower limb in a case where the band-like member is wrapped around the left lower limb such that the first electrode portion is guided to a third target position of the left lower limb and the second electrode portion is guided to a fourth target position of the left lower limb.

In the electrical treatment device according to the present disclosure described above, preferably the belt-like member has a length direction corresponding to a circumferential direction in the wrapped state and a width direction orthogonal to the length direction. In this case, the first mark portion may be provided on either a first end side or a second end side of the band-like member in the width direction, and the second mark portion may be provided on either the first end side or the second end side of the band-like member in the width direction.

In the electrical treatment device according to the present disclosure described above, preferably the band-like member has a length direction corresponding to a circumferential direction in the wrapped state and a width direction orthogonal to the length direction. In this case, the first mark portion and the second mark portion may be disposed offset in the length direction.

In the electrical treatment device according to the present disclosure described above, preferably the first electrode portion is provided, relative to a middle axis passing through a middle portion between the first mark portion and the second mark portion in the length direction and extending in the width direction, on a side where the first mark portion is positioned, and preferably the second electrode portion is provided, relative to the middle axis, on a side where the second mark portion is positioned.

In the electrical treatment device according to the present disclosure described above, preferably an end portion of the first electrode portion positioned closer to the second mark portion is positioned on a first center line passing through a center of the first mark portion in the width direction or, relative to the first center line, on a side opposite to a side where the second electrode portion is positioned, and preferably an end portion of the second electrode portion positioned closer to the first mark portion is positioned on a second center line passing through a center of the second mark portion in the width direction or, relative to the second center line, on a side opposite to a side where the first electrode portion is positioned.

In the electrical treatment device according to the present disclosure described above, preferably the band-like member includes a first main surface facing the body surface of the user in the wrapped state and a second main surface positioned on a side opposite to the first main surface. In this case, the first mark portion and the second mark portion may be provided on the second main surface.

The electrical treatment device according to the present disclosure described above may further include a main body portion including a current supply portion configured to supply a current to the first electrode portion and the second electrode portion and a case configured to accommodate the current supply portion in an interior of the case. In this case, preferably the case is disposed on the second main surface. Preferably, the band-like member has a length direction corresponding to a circumferential direction in the wrapped state. Further, preferably an end portion on a first side of the case in a first direction parallel to the length direction is configured to recede from the second main face as proximity toward the first side in the first direction increases, and preferably an end portion on a second side of the case in the first direction is configured to recede from the second main surface as proximity toward the second side in the first direction increases. Furthermore, preferably the first mark portion is provided on the second main surface in a portion overlapping with the end portion on the first side of the case when the case is viewed from the front, and the second mark portion is provided on the second main surface in a portion overlapping with the end portion on the second side of the case when the case is viewed from the front.

The electrical treatment device according to the present disclosure described above may further include a main body portion including a current supply portion configured to supply a low frequency current to the first electrode portion and the second electrode portion and a case configured to accommodate the current supply portion in an interior of the case. In this case, preferably the band-like member includes a first main surface facing the body surface of the user in the wrapped state and a second main surface positioned on a side opposite to the first main surface, and preferably the case is disposed on the second main surface. The first mark portion and the second mark portion may be provided on the main body portion.

In the electrical treatment device according to the present disclosure described above, the first mark portion and the second mark portion may be provided on a surface of the case in a portion different from a facing surface of the case facing the second main surface.

In the electrical treatment device according to the present disclosure described above, preferably the first mark portion and the second mark portion differ in design from each other.

In the electrical treatment device according to the present disclosure described above, preferably, in the wrapped state, a dermatome in contact with the first electrode portion on the body surface of the user and a dermatome in contact with the second electrode portion on the body surface of the user differ.

In the electrical treatment device according to the present disclosure described above, preferably, in a first wrapped state obtained by wrapping the band-like member below a right knee such that the first mark portion overlaps with a first virtual line passing through a center of a right patella in a length direction of the right lower limb when viewed from the front of the user, an upper end of the first electrode portion and an upper end of the second electrode portion are positioned 10 mm below a lower end of the right patella, an end portion of the first electrode portion positioned closer to the second mark portion overlaps with the first virtual line, and an end portion of the second electrode portion positioned closer to the first mark portion is positioned 30 mm away from an end portion of the first electrode portion positioned closer to the second mark portion toward an inner side of the right lower limb. Further, in a second wrapped state obtained by wrapping the band-like member below a left knee such that the second mark portion overlaps with a second virtual line passing through a center of a left patella in a length direction of the left lower limb when viewed from the front of the user, the upper end of the first electrode portion and the upper end of the second electrode portion are positioned 10 mm below a lower end of the left patella, an end portion of the second electrode portion positioned closer to the first mark portion overlaps with the second virtual line, and the end portion of the first electrode portion positioned closer to the second mark portion is positioned 30 mm away from the end portion of the second electrode portion positioned closer to the first mark portion toward an inner side of the left lower limb.

Advantageous Effects of Invention

According to the present disclosure, it is possible to provide an electrical treatment device capable of bringing an electrode portion into contact with an appropriate location on a body surface, even when used for both a left lower limb and a right lower limb.

DESCRIPTION OF EMBODIMENTS

Figure 1:
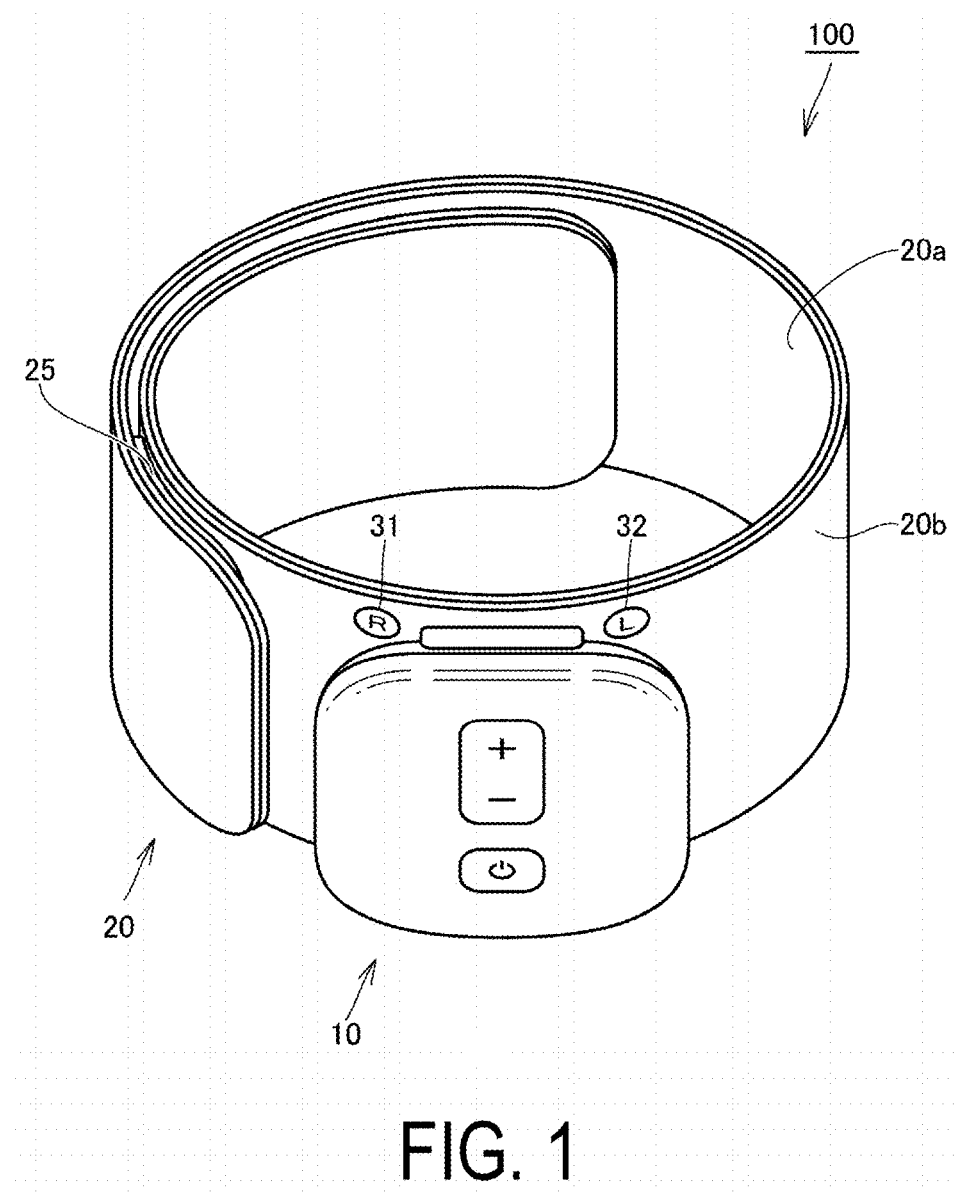
FIG. 1 is a perspective view illustrating a wrapped state of an electrical treatment device according to an embodiment.

Embodiments of the present disclosure will be described in detail below with reference to the drawings. Note that in the following embodiments, identical or common components are given the same reference signs in the drawings, and the descriptions thereof are not repeated.

Figure 2:
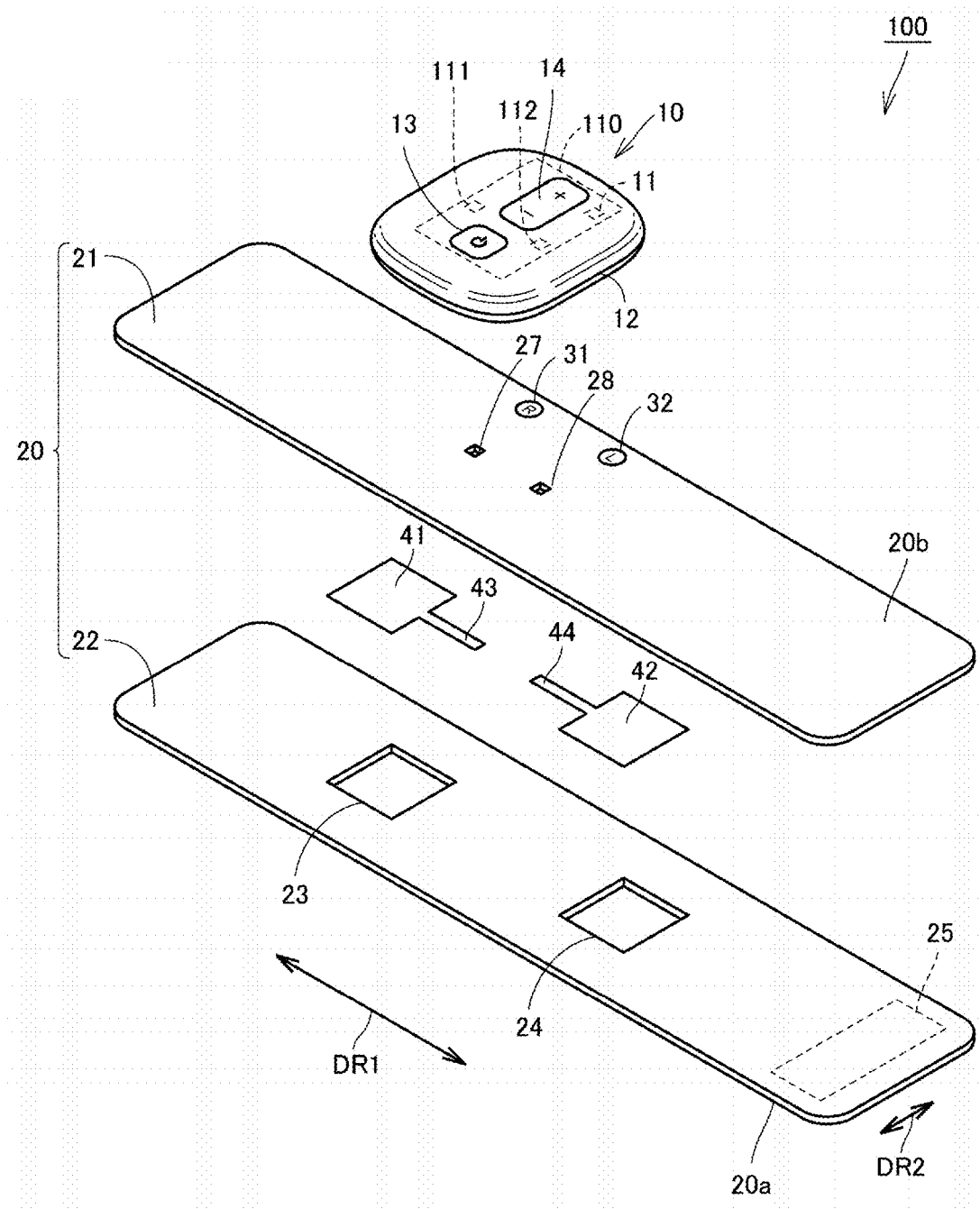
FIG. 2 is an exploded perspective view illustrating the electrical treatment device according to the embodiment.

FIG. 1 is a perspective view illustrating a wrapped state of an electrical treatment device according to an embodiment. FIG. 2 is an exploded perspective view illustrating the electrical treatment device according to the embodiment. An electrical treatment device 100 according to the embodiment will be described with reference to FIG. 1 and FIG. 2.

As illustrated in FIG. 1 and FIG. 2, the electrical treatment device 100 according to the embodiment includes a main body portion 10, a band-like member 20, a first electrode portion 41, a second electrode portion 42, a first mark portion 31, and a second mark portion 32.

The electrical treatment device 100 is, for example, a low-frequency treatment device configured to relieve pain in a right lower limb or a left lower limb of a user by supplying a low-frequency pulse current to the first electrode portion 41 and the second electrode portion 42 that are in contact with a body surface of the user. The frequency of the low-frequency pulse current is, for example, from 1 Hz to 1,200 Hz.

The band-like member 20 is configured to be wrappable around both the right lower limb and the left lower limb of the user. The band-like member 20 has a long shape prior to being wrapped around the user. The band-like member 20 has a substantially rectangular shape when viewed planarly.

The band-like member 20 has a length direction (direction DR1) corresponding to a circumferential direction in a wrapped state obtained by being wrapped around the right lower limb or the left lower limb, and a width direction (direction DR2) orthogonal to the length direction. The band-like member 20 includes a first main surface 20a facing the body surface of the user in the wrapped state, and a second main surface 20b positioned on a side opposite to the first main surface 20a.

The band-like member 20 includes a first member 21 and a second member 22. The first member 21 and the second member 22 have flexibility. The first member 21 is a member constituting an outer circumferential side of the band-like member 20 in the wrapped state. A surface of the first member 21 corresponding to the outer circumferential side in the wrapped state (the second main surface 20b of the band-like member 20) is configured to be capable of fastening a surface fastener 25 described later. The first member 21 is provided with opening portions 27, 28 at positions corresponding to a first terminal 111 and a second terminal 112 of the main body portion 10 described later.

The second member 22 is a member constituting an inner circumferential side of the band-like member 20 in the wrapped state. A surface of the second member 22 corresponding to the inner circumferential side in the wrapped state (the first main surface 20a of the band-like member 20) is provided with the surface fastener 25. In the wrapped state, the surface fastener 25 is fastened with the second main surface 20b, thereby fixing the band-like member 20 to the right lower limb or the left lower limb.

The second member 22 is provided with window portions 23, 24 at positions corresponding to the first electrode portion 41 and the second electrode portion 42. With the window portions 23, 24 provided, the first electrode portion 41 and the second electrode portion 42 can be brought into contact with the body surface of the user in the wrapped state.

The main body portion 10 is fixed to the band-like member 20. The main body portion 10 is positioned on the second main surface 20b side of the band-like member 20. The main body portion 10 includes a current supply portion 11 and a case 12. The current supply portion 11 supplies current to the first electrode portion 41 and the second electrode portion 42. The current supply portion 11 is mounted on a circuit board 110.

The circuit board 110 is provided with a control unit configured to control the operation of each portion of the electrical treatment device 100. The circuit board 110 is provided with the first terminal 111 and the second terminal 112. The first terminal 111 is electrically connected to the first electrode portion 41 via a wire portion 43 described later. The second terminal 112 is electrically connected to the second electrode portion 42 via a wire portion 44 described later.

The case 12 has a box shape. The case 12 accommodates the current supply portion 11 and the circuit board 110 in an interior thereof. The case 12 is disposed on the second main surface 20b of the band-like member 20.

An end portion on a first side of the case 12 in a first direction parallel to the length direction is configured to recede from the second main surface 20b as proximity toward the first side in the first direction increases. As a result, a gap is formed between the end portion on the first side of the case 12 and the second main surface 20b.

An end portion on a second side of the case 12 in the first direction parallel to the length direction is configured to recede from the second main surface 20b as proximity toward the second side in the first direction increases. As a result, a gap is formed between the end portion on the second side of the case 12 and the second main surface 20b.

A power button 13 and an adjustment button 14 for adjusting an electrical stimulation strength are provided on a front side of the case 12.

The first mark portion 31 is a mark configured to be aligned with a specific position of the right lower limb when the band-like member 20 is wrapped around the right lower limb such that the first electrode portion 41 is guided to a first target position of the right lower limb and the second electrode portion 42 is guided to a second target position on the right lower limb.

The second mark portion 32 is a mark configured to be aligned with a specific position of the left lower limb when the band-like member 20 is wrapped around the left lower limb such that the first electrode portion 41 is guided to a third target position of the left lower limb and the second electrode portion 42 is guided to a fourth target position on the left lower limb.

The first mark portion 31 and the second mark portion 32 are provided on the second main surface 20b of the band-like member 20. As a result, when the user wraps the band-like member 20, the first mark portion 31 and the second mark portion 32 can be easily visually recognized. As a result, the first mark portion 31 or the second mark portion 32 can be easily aligned with the specific position, as described later.

The first mark portion 31 and the second mark portion 32 are provided on a first end side of the band-like member 20 in the width direction. The first mark portion 31 and the second mark portion 32 are disposed offset in the length direction of the band-like member 20. The first mark portion 31 and the second mark portion 32 are disposed side by side in the length direction of the band-like member 20.

The first mark portion 31 is provided on the second main surface 20b in a portion overlapping with the end portion on the first side of the case 12 when the case 12 is viewed from the front. As described above, a gap is formed between the end portion on the first side of the case 12 and the second main surface 20b. The gap allows the user to visually recognize the first mark portion 31 when the band-like member 20 is wrapped. As a result, during wrapping, the first mark portion 31 can be aligned with the specific position on the right lower limb. On the other hand, when viewed from the front, the first mark portion 31 is hidden by the case 12, and thus a design quality can be enhanced.

The second mark portion 32 is provided on the second main surface 20b in a portion overlapping with the end portion on the second side of the case 12 when the case 12 is viewed from the front. As described above, a gap is formed between the end portion on the second side of the case 12 and the second main surface 20b. The gap allows the user to visually recognize the second mark portion 32 when the band-like member 20 is wrapped. As a result, during wrapping, the second mark portion 32 can be aligned with the specific position on the left lower limb. On the other hand, when viewed from the front, the second mark portion 32 can be hidden by the case 12, and thus a design quality can be enhanced.

The design of the first mark portion 31 and the design of the second mark portion 32 are different from each other. The first mark portion 31 has a design in which, for example, an outline of the letter R is placed on a background of an orange circle. The second mark portion 32 has a design in which, for example, an outline of the letter L is placed on a background of a light blue circle.

Note that the first mark portion 31 and the second mark portion 32 are not limited to such designs, and can be changed as appropriate as long as distinguished. For example, the first mark portion 31 and the second mark portion 32 may be formed so as to differ in shape from each other, or may be formed so as to differ in color from each other.

The first mark portion 31 and the second mark portion 32 may be formed by being printed on the second main surface 20b, or may be formed by bonding a structure.

The first electrode portion 41 and the second electrode portion 42 each have a polygonal shape. Note that the polygonal shape also includes shapes with rounded corners. The first electrode portion 41 and the second electrode portion 42 each have, for example, a square shape. In the first electrode portion 41 and the second electrode portion 42, a length parallel to the length direction of the band-like member 20 is 40 mm, for example, and a length parallel to the width direction of the band-like member 20 is 40 mm, for example.

Note that the first electrode portion 41 and the second electrode portion 42 are not limited to a polygonal shape, and may have an oval shape, such as an elliptical shape, a long circular shape, or a racetrack shape, or a circular shape.

The first electrode portion 41 and the second electrode portion 42 are fixed to the first member 21 of the band-like member 20. Specifically, the first electrode portion 41 and the second electrode portion 42 are fixed to a surface of the first member 21 in a portion facing the second member 22.

The first electrode portion 41 and the second electrode portion 42 are disposed side by side in the length direction. The first electrode portion 41 and the second electrode portion 42 are exposed through the window portions 23, 24 of the second member 22. Thus, the first electrode portion 41 and the second electrode portion 42 can be brought into contact with the body surface of the user in the wrapped state.

The first electrode portion 41 and the second electrode portion 42 are electrode portions for running a current to the user. With the first electrode portion 41 and the second electrode portion 42 in contact with the body surface of the user, a current is supplied to the first electrode portion 41 and the second electrode portion 42, making it possible to deliver a current to the user.

The first electrode portion 41 and the second electrode portion 42 are electrically connected to the first terminal 111 and the second terminal 112 of the main body portion 10 via the wire portion 43 and the wire portion 44.

A first end of the wire portion 43 in the length direction is connected to the first electrode portion 41. A second end of the wire portion 43 in the length direction is connected to the first terminal 111. A first end of the wire portion 44 in the length direction is connected to the second terminal 112. A second end of the wire portion 44 in the length direction is connected to the second electrode portion 42.

Figure 3:
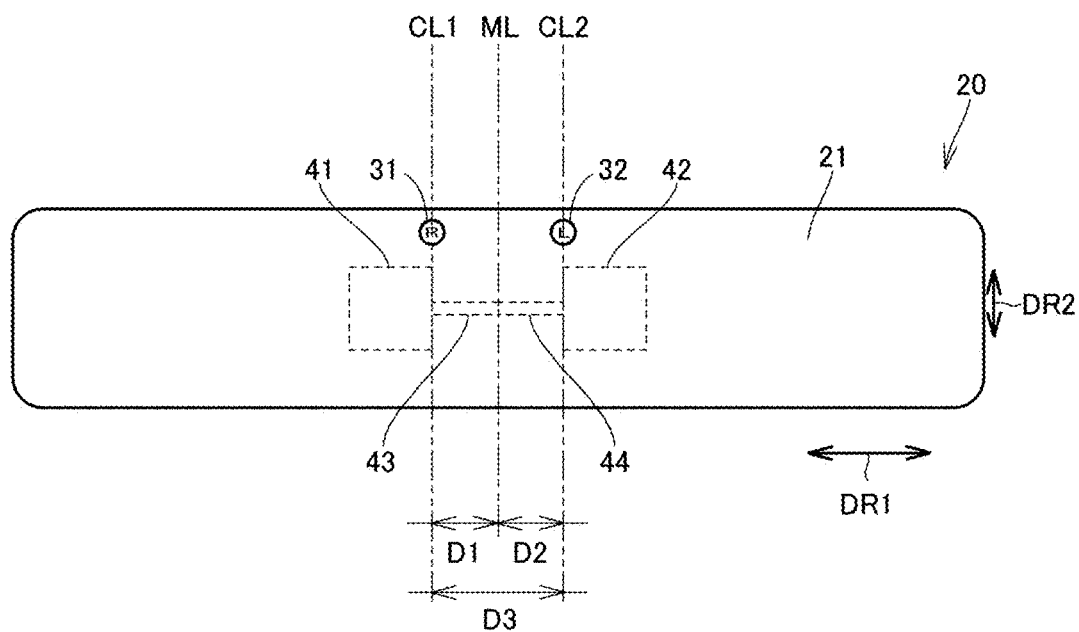
FIG. 3 is a plan view illustrating a positional relationship between a first mark portion, a second mark portion, a first electrode portion, and a second electrode portion of the electrical treatment device according to the embodiment.

FIG. 3 is a plan view illustrating a positional relationship between the first mark portion, the second mark portion, the first electrode portion, and the second electrode portion of the electrical treatment device according to the embodiment. The positional relationship between the first mark portion 31, the second mark portion 32, the first electrode portion 41, and the second electrode portion 42 will be described with reference to FIG. 3.

As illustrated in FIG. 3, the first electrode portion 41 is provided, relative to a middle axis ML passing through a middle portion between the first mark portion 31 and the second mark portion 32 in the length direction and extending in the width direction, on a side where the first mark portion 31 is positioned.

For example, an end portion of the first electrode portion 41 positioned closer to the second mark portion 32 is positioned on a first center line CL1 passing through a center of the first mark portion 31 in the width direction or, relative to the first center line CL1, on a side opposite to a side where the second electrode portion 42 is positioned.

The second electrode portion 42 is provided, relative to the middle axis ML, on a side where the second mark portion 32 is positioned. For example, an end portion of the second electrode portion 42 positioned closer to the first mark portion 31 is positioned on a second center line CL2 passing through a center of the second mark portion 32 in the width direction or, relative to the second center line CL2, on a side opposite to a side where the first electrode portion 41 is positioned.

With the first electrode portion 41 and the second electrode portion 42 thus disposed, the first electrode portion 41 and the second electrode portion 42 are easily guided to different dermatomes in the wrapped state, as described later.

For example, a distance D1 in the length direction between the end portion of the first electrode portion 41 positioned closer to the second mark portion 32 and the middle axis ML, and a distance D2 in the length direction between the end portion of the second electrode portion 42 positioned closer to the first mark portion 31 and the middle axis ML are equal.

Note that the first electrode portion 41 and the second electrode portion 42 may be provided at positions asymmetrical relative to the middle axis ML.

A distance in the length direction between the end portion of the first electrode portion 41 positioned closer to the second mark portion 32 and the end portion of the second electrode portion 42 positioned closer to the first mark portion 31 is, for example, 30 mm.

Figure 4:
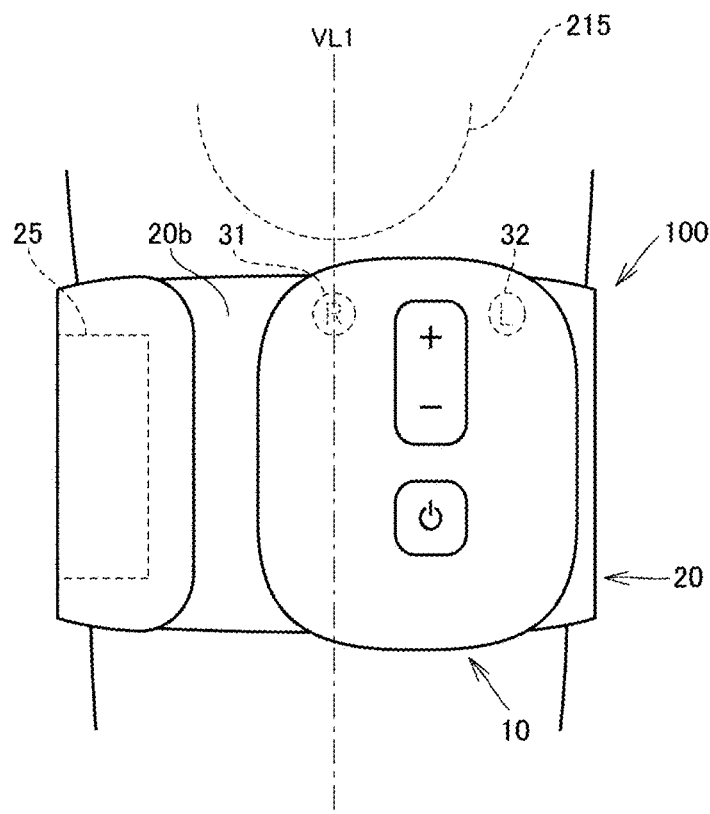
FIG. 4 is a drawing illustrating a wrapped state obtained by wrapping the electrical treatment device according to the embodiment below a right knee.
Figure 5:
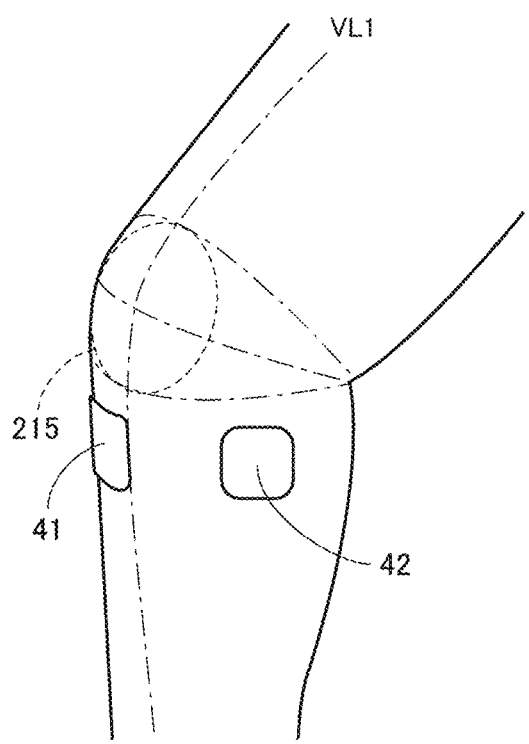
FIG. 5 is a drawing illustrating positions where the first electrode portion and the second electrode portion come into contact with a body surface in the wrapped state illustrated in FIG. 4.

FIG. 4 is a drawing illustrating a wrapped state obtained by wrapping the electrical treatment device according to the embodiment below the right knee. FIG. 5 is a drawing illustrating positions where the first electrode portion and the second electrode portion come into contact with the body surface in the wrapped state illustrated in FIG. 4. The wrapped state obtained by wrapping the electrical treatment device 100 below the right knee will be described with reference to FIG. 4 and FIG. 5.

As illustrated in FIG. 4, when the electrical treatment device 100 is wrapped below the right knee, the band-like member 20 is wrapped so that the first mark portion 31 overlaps with a first virtual line VL1 passing through a center of a right patella 215 in the length direction of the right lower limb when viewed from the front of the user and, in this state, the surface fastener 25 is fastened to the second main surface 20b.

With the first mark portion 31 aligned so as to overlap with the first virtual line VL1, the first electrode portion 41 is guided to the first target position, and the second electrode portion 42 is guided to the second target position.

Specifically, when viewed from the front of the user, the first electrode portion 41 is guided so that an upper end is positioned 10 mm below a lower end of the right patella 215, and the end portion positioned closer the second mark portion 32 is on the first virtual line VL1 or near the first virtual line VL1.

When viewed from the front of the user, the second electrode portion 42 is guided so that an upper end is positioned 10 mm below the lower end of the right patella 215, and the end portion positioned closer to the first mark portion 31 is positioned 30 mm away from the end portion of the first electrode portion 41 positioned closer to the second mark portion 32 toward an inner side of the right lower limb.

Figure 6:
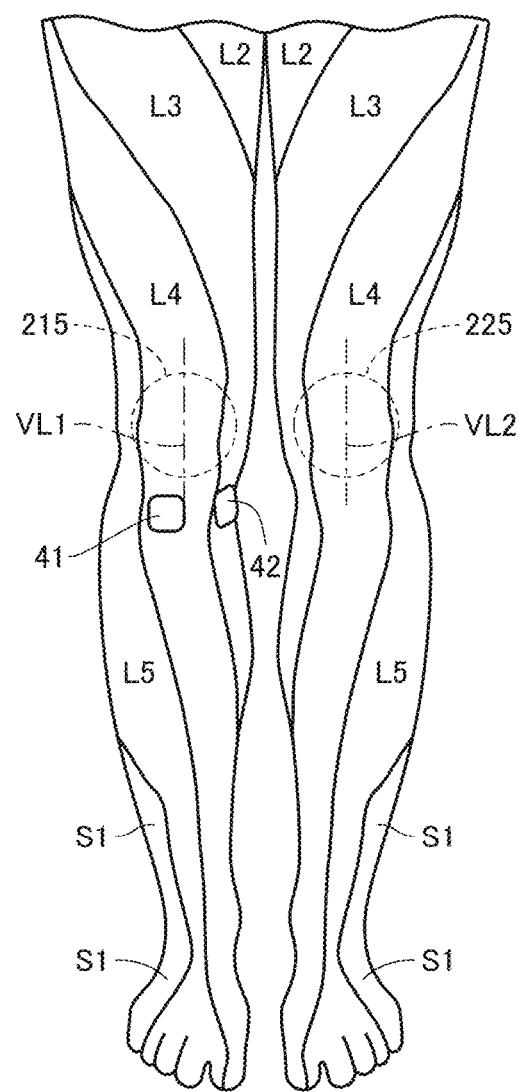
FIG. 6 is a drawing illustrating a relationship between the positions where the first electrode portion and the second electrode portion come into contact with the body surface in the wrapped state illustrated in FIG. 4 and dermatomes.

FIG. 6 is a drawing illustrating a relationship between the positions where the first electrode portion and the second electrode portion come into contact with the body surface in the wrapped state illustrated in FIG. 4 and dermatomes.

The surface of the skin is known to be divided into specific areas called dermatomes (skin sensory zones). In the lower limb, the surface of the skin is divided into dermatomes L2 to L5 and S1, as illustrated in FIG. 6. Each area is controlled by sensory nerve fibers of one spinal nerve root, and sensory information in each area is transmitted to a specific spinal nerve root by the sensory nerve fibers.

With the first mark portion 31 aligned so as to overlap with the first virtual line VL1, the first electrode portion 41 and the second electrode portion 42 come into contact with different dermatomes on the body surface of the user in the wrapped state. Specifically, the first electrode portion 41 comes into contact with the dermatome L4 corresponding to the first target position, and the second electrode portion 42 comes into contact with the dermatome L3 corresponding to the second target position. That is, the dermatome in contact with the first electrode portion 41 and the dermatome in contact with the second electrode portion 42 are different from each other. In a case where a current is caused to flow with the first electrode portion 41 and the second electrode portion 42 in contact with different dermatomes, treatment can be effectively performed.

Note that the first electrode portion 41 preferably comes into contact with the dermatome L4 in its entirety, but may partially come into contact with the dermatome L5 as long as a major portion comes into contact with the dermatome L4.

In a case where a current is caused to flow with the first electrode portion 41 and the second electrode portion 42 in contact with the body surface of the user so as to be disposed at positions such as described above, it is possible to effectively achieve a pain relief effect.

Figure 7:
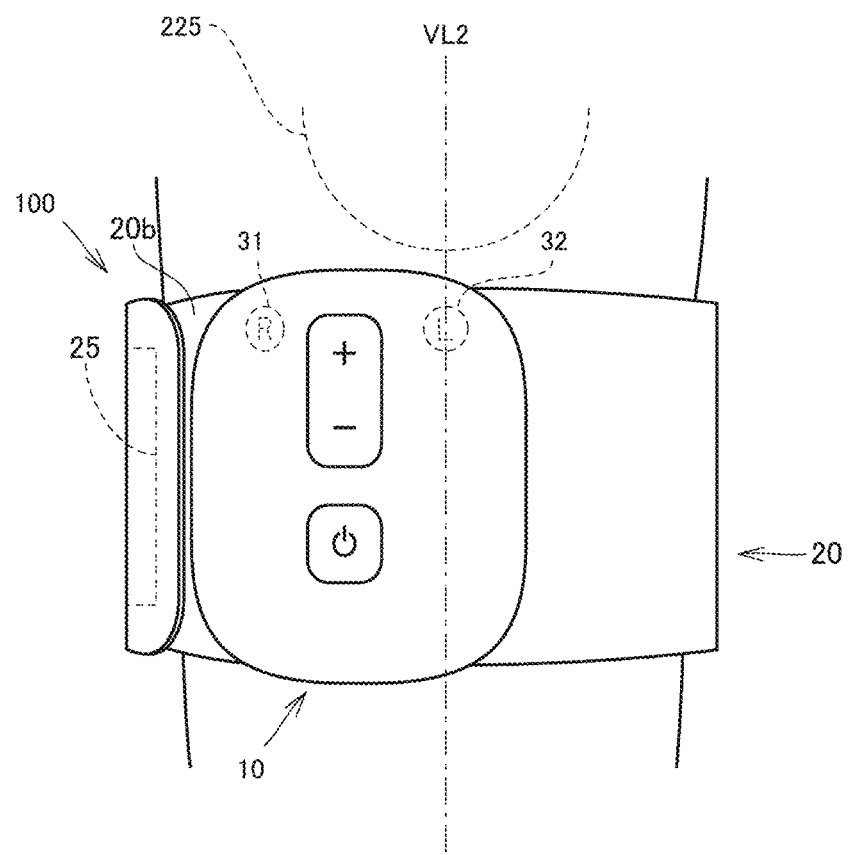
FIG. 7 is a drawing illustrating a wrapped state obtained by wrapping the electrical treatment device according to the embodiment below a left knee.
Figure 8:
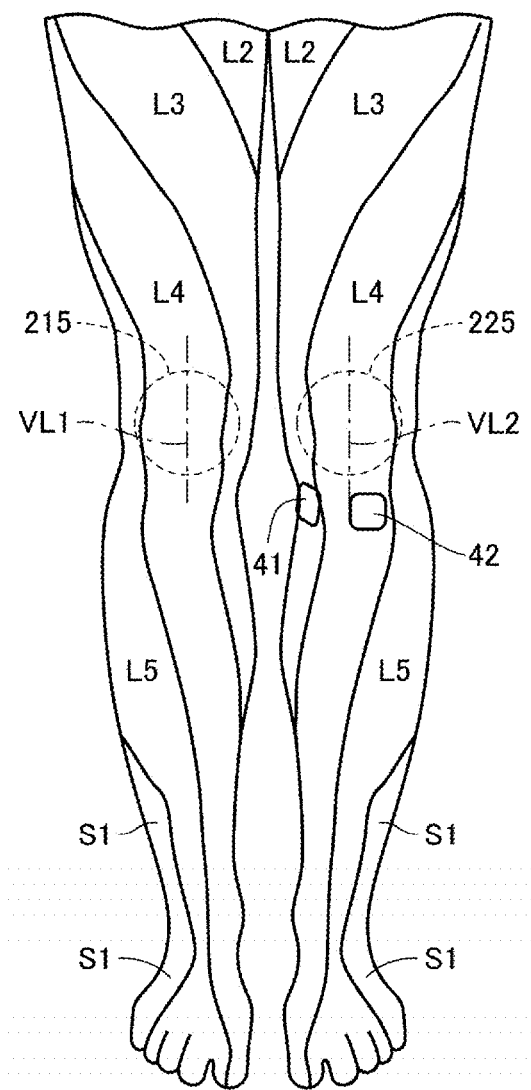
FIG. 8 is a drawing illustrating a relationship between the positions where the first electrode portion and the second electrode portion come into contact with the body surface in the wrapped state illustrated in FIG. 7 and dermatomes.

FIG. 7 is a drawing illustrating a wrapped state obtained by wrapping the electrical treatment device according to the embodiment below the left knee. FIG. 8 is a drawing illustrating a relationship between the positions where the first electrode portion and the second electrode portion come into contact with the body surface in the wrapped state illustrated in FIG. 7 and dermatomes. The wrapped state obtained by wrapping the electrical treatment device 100 below the left knee will be described with reference to FIG. 7 and FIG. 8.

As illustrated in FIG. 7, when the electrical treatment device 100 is wrapped below the left knee, the band-like member 20 is wrapped so that the second mark portion 32 overlaps with a second virtual line VL2 passing through a center of a left patella 225 in the length direction of the left lower limb when viewed from the front of the user and, in this state, the surface fastener 25 is fastened to the second main surface 20b.

With the second mark portion 32 aligned so as to overlap with the second virtual line VL2, the first electrode portion 41 is guided to the third target position, and the second electrode portion 42 is guided to the fourth target position.

Specifically, as illustrated in FIG. 8, when viewed from the front of the user, the second electrode portion 42 is guided so that an upper end is positioned 10 mm below a lower end of the left patella 225, and the end portion positioned closer to the first mark portion 31 is on the second virtual line VL2 or near the second virtual line VL2.

When viewed from the front of the user, the first electrode portion 41 is guided so that an upper end is positioned 10 mm below the lower end of the left patella 225, and the end portion positioned closer to the second mark portion 32 is positioned 30 mm away from the end portion of the second electrode portion 42 positioned closer to the first mark portion 31 toward an inner side of the left lower limb.

With the second mark portion 32 aligned so as to overlap with the second virtual line VL2, the first electrode portion 41 and the second electrode portion 42 come into contact with different dermatomes on the body surface of the user in the wrapped state. Specifically, the second electrode portion 42 comes into contact with the dermatome L4 corresponding to the fourth target position, and the first electrode portion 41 comes into contact with the dermatome L3 corresponding to the third target position. In a case where a current is caused to flow with the first electrode portion 41 and the second electrode portion 42 in contact with different dermatomes, treatment can be effectively performed.

Note that the second electrode portion 42 preferably comes into contact with the dermatome L4 in its entirety, but may partially come into contact with the dermatome L5 as long as a major portion comes into contact with the dermatome L4.

In a case where a current is caused to flow with the first electrode portion 41 and the second electrode portion 42 in contact with the body surface of the user so as to be disposed at positions such as described above, it is possible to effectively achieve a pain relief effect.

As described above, in the electrical treatment device 100 according to the present embodiment, when the band-like member 20 is wrapped around the right lower limb, the first mark portion 31 is aligned with the specific position of the right lower limb, making it possible to guide the first electrode portion 41 to the first target position of the right lower limb and guide the second electrode portion 42 to the second target position on the right lower limb. Further, when the band-like member 20 is wrapped around the left lower limb, the second mark portion 32 is aligned with the specific position of the left lower limb, making it possible to guide the first electrode portion 41 to the third target position of the left lower limb and guide the second electrode portion 42 to the fourth target position on the left lower limb. Accordingly, the electrode portions of the electrical treatment device 100 can be bought into contact with appropriate locations on the body surface, even when the electrical treatment device 100 is used for both the left lower limb and the right lower limb.

OTHER MODIFIED EXAMPLES

In the embodiment described above, a case where the band-like member 20 is wrapped below the knee has been illustrated and described; however, no such limitation is intended. Within a range that does not depart from the spirit of the present invention, the band-like member 20 may be wrapped around a thigh, or may be wrapped around a shin.

In the embodiment described above, a case where the first mark portion 31 and the second mark portion 32 are provided on the second main surface 20*b* of the band-like member 20 has been illustrated and described; however, no such limitation is intended, and the first mark portion 31 and the second mark portion 32 may be provided to the main body portion 10. In this case, the first mark portion 31 and the second mark portion 32 may be provided on a surface of the case 12 in a portion different from a facing surface of the case 12 facing the second main surface 20*b*. When provided at such positions, the first mark portion 31 and the second mark portion 32 are easily visually recognized by the user, and the alignment of the first mark portion 31 or the second mark portion 32 can be easily performed.

In the embodiment described above, a case where the first mark portion 31 and the second mark portion 32 are printed or bonded to the second main surface 20*b* has been illustrated and described; however, no such limitation is intended, and the first mark portion 31 and the second mark portion 32 may be constituted by a light source such as a lamp.

In the embodiment described above, a case where the first mark portion 31 and the second mark portion 32 are provided on the first end side of the band-like member in the width direction has been illustrated and described; however, no such limitation is intended. The first mark portion 31 may be provided on either the first end side or the second end side of the band-like member 20 in the width direction, and the second mark portion 32 may be provided on either the first end side or the second end side of the band-like member in the width direction.

For example, in a case where the first mark portion 31 is provided on the first end side of the band-like member 20 in the width direction, and the second mark portion 32 is provided on the second end side of the band-like member 20 in the width direction, when the band-like member 20 is wrapped around the right lower limb, the first mark portion 31 is aligned with a specific position (below the right patella, for example) with the first mark portion 31 positioned on the upper side and the second mark portion 32 positioned on the lower side. On the other hand, when the band-like member 20 is wrapped around the left lower limb, the band-like member 20 is turned upside down, and the second mark portion 32 is aligned with a specific position (below the left patella, for example) with the second mark portion 32 positioned on the upper side and the first mark portion 31 positioned on the lower side. In such aspects as well, the distinctive portions described in the embodiments can be combined as appropriate.

SUPPLEMENTARY NOTES

As described above, the present embodiment includes disclosures such as described below.

Configuration 1

An electrical treatment device (100) including a band-like member (20) configured to be wrappable around both a right lower limb and a left lower limb of a user, a first electrode portion (41) and a second electrode portion (42) supported by the band-like member (20) such that the first electrode portion (41) and the second electrode portion (42) come into contact with a body surface of the user in a wrapped state obtained by wrapping the band-like member (20) around the right lower limb or the left lower limb, and configured to deliver a current to the user, a first mark portion (31) configured to be aligned with a specific position of the right lower limb when the band-like member (20) is wrapped around the right lower limb such that the first electrode portion (41) is guided to a first target position of the right lower limb and the second electrode portion (42) is guided to a second target position of the right lower limb, and a second mark portion (32) configured to be aligned with a specific position of the left lower limb when the band-like member (20) is wrapped around the left lower limb such that the first electrode portion (41) is guided to a third target position of the left lower limb and the second electrode portion (42) is guided to a fourth target position of the left lower limb.

Configuration 2

The electrical treatment device according to Configuration 1, wherein the band-like member (20) has a length direction corresponding to a circumferential direction in the wrapped state, and a width direction orthogonal to the length direction, the first mark portion (31) is provided on either a first end side or a second end side of the band-like member (20) in the width direction, and the second mark portion (32) is provided on either the first end side or the second end side of the band-like member (20) in the width direction.

Configuration 3

The electrical treatment device (100) according to Configuration 1 or 2, wherein the first mark portion (31) and the second mark portion (32) are disposed offset in the length direction.

Configuration 4

The electrical treatment device (100) according to Configuration 3, wherein the first electrode portion (41) is provided, relative to a middle axis passing through a middle portion between the first mark portion (31) and the second mark portion (32) in the length direction and extending in the width direction, on a side where the first mark portion (31) is positioned, and the second electrode portion (42) is provided, relative to the middle axis, on a side where the second mark portion (32) is positioned.

Configuration 5

The electrical treatment device (100) according to Configuration 4, wherein an end portion of the first electrode portion (41) positioned closer to the second mark portion (32) is positioned on a first center line passing through a center of the first mark portion (31) in the width direction or, relative to the first center line, on a side opposite to a side where the second electrode portion (42) is positioned, and an end portion of the second electrode portion (42) positioned closer to the first mark portion (31) is positioned on a second center line passing through a center of the second mark portion (32) in the width direction or, relative to the second center line, on a side opposite to a side where the first electrode portion (41) is positioned.

Configuration 6

The electrical treatment device (100) according to any one of Configurations 1 to 5, wherein the band-like member (20) includes a first main surface (20*a*) facing the body surface of the user in the wrapped state, and a second main surface (20b) positioned on a side opposite to the first main surface (20a), and the first mark portion (31) and the second mark portion (32) are provided on the second main surface (20b).

Configuration 7

The electrical treatment device (100) according to Configuration 6, further including a main body portion (10) including a current supply portion (11) configured to supply a current to the first electrode portion (41) and the second electrode portion (42), and a case (12) configured to accommodate the current supply portion (11) in an interior of the case (12), wherein the case (12) is disposed on the second main surface (20b), an end portion on a first side of the case (12) in a first direction parallel to the length direction is configured to recede from the second main face (20b) as proximity toward the first side in the first direction increases, an end portion on a second side of the case (12) in the first direction is configured to recede from the second main surface (20b) as proximity toward the second side in the first direction increases, the first mark portion (31) is provided on the second main surface (20b) in a portion overlapping with the end portion on the first side of the case (12) when the case (12) is viewed from the front, and the second mark portion (32) is provided on the second main surface (20b) in a portion overlapping with the end portion on the second side of the case (12) when the case (12) is viewed from the front.

Configuration 8

The electrical treatment device (100) according to any one of Configurations 1 to 5, further including a main body portion (10) including a current supply portion (11) configured to supply a current to the first electrode portion (41) and the second electrode portion (42), and a case (12) configured to accommodate the current supply portion (11) in an interior of the case (12), wherein the band-like member (20) includes a first main surface (20a) facing the body surface of the user in the wrapped state, and a second main surface (20b) positioned on a side opposite to the first main surface (20a), the case (12) is disposed on the second main surface (20b), and the first mark portion (31) and the second mark portion (32) are provided to the main body portion (10).

Configuration 9

The electrical treatment device (100) according to Configuration 8, wherein the first mark portion (31) and the second mark portion (32) are provided on a surface of the case (12) in a portion different from a facing surface of the case (12) facing the second main surface (20b).

Configuration 10

The electrical treatment device (100) according to any one of Configurations 1 to 9, wherein the first mark portion (31) and the second mark portion (32) differ in design from each other.

Configuration 11

The electrical treatment device according to any one of Configurations 1 to 10, wherein in the wrapped state, a dermatome in contact with the first electrode portion (41) on the body surface of the user and a dermatome in contact with the second electrode portion (42) on the body surface of the user differ.

Configuration 12

The electrical treatment device according to any one of Configurations 1 to 10, wherein in a first wrapped state obtained by wrapping the band-like member (20) below a right knee such that the first mark portion (31) overlaps with a first virtual line passing through a center of a right patella in a length direction of the right lower limb when viewed from the front of the user, an upper end of the first electrode portion (41) and an upper end of the second electrode portion (42) are positioned 10 mm below a lower end of the right patella, an end portion of the first electrode portion (41) positioned closer to the second mark portion (32) overlaps with the first virtual line, and an end portion of the second electrode portion (42) positioned closer to the first mark portion (31) is positioned 30 mm away from an end portion of the first electrode portion (41) positioned closer to the second mark portion (32) toward an inner side of the right lower limb, and in a second wrapped state obtained by wrapping the band-like member (20) below a left knee such that the second mark portion (32) overlaps with a second virtual line passing through a center of a left patella in a length direction of the left lower limb when viewed from the front of the user, the upper end of the first electrode portion (41) and the upper end of the second electrode portion (42) are positioned 10 mm below a lower end of the left patella, an end portion of the second electrode portion (42) positioned closer to the first mark portion (31) overlaps with the second virtual line, and the end portion of the first electrode portion (41) positioned closer to the second mark portion (32) is positioned 30 mm away from the end portion of the second electrode portion (42) positioned closer to the first mark portion (31) toward an inner side of the left lower limb.

The embodiments described herein are illustrative in all respects and are not intended as limitations. The scope of the present invention is indicated by the claims and includes all meaning equivalent to the scope and changes within the scope.

REFERENCE SIGNS LIST

10 Main body portion
11 Current supply portion
12 Case
13 Power button
14 Adjustment button
20 Band-like member
20a First main surface
20b Second main surface
21 First member
22 Second member
23, 24 Window portion
25 Surface fastener
27, 28 Opening portion
31 First mark portion
32 Second mark portion
41 First electrode portion
42 Second electrode portion
43, 44 Wire portion
100 Electrical treatment device
110 Circuit board
111 First terminal
112 Second terminal
215 Right patella
225 Left patella

The invention claimed is:

1. An electrical treatment device comprising:
a band-like member configured to be wrappable around both a right lower limb and a left lower limb of a user;
a first electrode portion and a second electrode portion supported by the band-like member such that the first electrode portion and the second electrode portion come into contact with a body surface of the user in a wrapped state obtained by wrapping the band-like member around the right lower limb or the left lower limb, and configured to alleviate pain by delivering stimulation treatment via a current to the user;
a first mark portion configured to be aligned with a specific position of the right lower limb from a front side of the right lower limb when the band-like member is wrapped around the right lower limb such that the first electrode portion is guided to a first target position of the right lower limb and the second electrode portion is guided to a second target position of the right lower limb; and
a second mark portion configured to be aligned with a specific position of the left lower limb from a front side of the left lower limb when the band-like member is wrapped around the left lower limb such that the first electrode portion is guided to a third target position of the left lower limb and the second electrode portion is guided to a fourth target position of the left lower limb, wherein
the band-like member has a length direction corresponding to a circumferential direction in the wrapped state, and a width direction orthogonal to the length direction,
the band-like member has a first end portion and a second end portion in the width direction,
the first end portion is located on an upper side in the wrapped state,
the second end portion is located on a lower side in the wrapped state,
the first mark portion and the second mark portion are provided on the first end portion side of the band-like member in the width direction,
the first mark portion and the second mark portion are disposed offset in the length direction, and
the first mark portion and the second mark portion are provided so as to be visible from the outside when the band-like member is wrapped around the right lower limb or the left lower limb and in the wrapped state obtained by wrapping the band-like member around the right lower limb or the left lower limb.

2. The electrical treatment device according to claim 1, wherein
the first electrode portion is provided, relative to a middle axis passing through a middle portion between the first mark portion and the second mark portion in the length direction and extending in the width direction, on a side where the first mark portion is positioned, and
the second electrode portion is provided, relative to the middle axis, on a side where the second mark portion is positioned.

3. The electrical treatment device according to claim 2, wherein
an end portion of the first electrode portion positioned closer to the second mark portion is positioned on a first center line passing through a center of the first mark portion in the width direction or, relative to the first center line, on a side opposite to a side where the second electrode portion is positioned, and
an end portion of the second electrode portion positioned closer to the first mark portion is positioned on a second center line passing through a center of the second mark portion in the width direction or, relative to the second center line, on a side opposite to a side where the first electrode portion is positioned.

4. The electrical treatment device according to claim 1, wherein
the band-like member includes
a first main surface facing the body surface of the user in the wrapped state, and
a second main surface positioned on a side opposite to the first main surface, and
the first mark portion and the second mark portion are provided on the second main surface.

5. The electrical treatment device according to claim 4, further comprising:
a main body portion including
a current supply portion configured to supply a current to the first electrode portion and the second electrode portion, and
a case configured to accommodate the current supply portion in an interior of the case, wherein
the case is disposed on the second main surface,
an end portion on a first side of the case in a first direction parallel to the length direction is configured to recede from the second main face as proximity toward the first side in the first direction increases,
an end portion on a second side of the case in the first direction is configured to recede from the second main surface as proximity toward the second side in the first direction increases,
the first mark portion is provided on the second main surface in a portion overlapping with the end portion on the first side of the case when the case is viewed from the front, and
the second mark portion is provided on the second main surface in a portion overlapping with the end portion on the second side of the case when the case is viewed from the front.

6. The electrical treatment device according to claim 1, further comprising:
a main body portion including
a current supply portion configured to supply a current to the first electrode portion and the second electrode portion, and
a case configured to accommodate the current supply portion in an interior of the case, wherein
the band-like member includes
a first main surface facing the body surface of the user in the wrapped state, and
a second main surface positioned on a side opposite to the first main surface,
the case is disposed on the second main surface, and
the first mark portion and the second mark portion are provided to the main body portion.

7. The electrical treatment device according to claim 6, wherein
the first mark portion and the second mark portion are provided on a surface of the case in a portion different from a facing surface of the case facing the second main surface.

8. The electrical treatment device according to claim 1, wherein
the first mark portion and the second mark portion differ in design from each other.

9. The electrical treatment device according to claim 1, wherein
in the wrapped state, a dermatome in contact with the first electrode portion on the body surface of the user and a dermatome in contact with the second electrode portion on the body surface of the user differ.

10. The electrical treatment device according to claim 1, wherein
in a first wrapped state obtained by wrapping the band-like member below a right knee such that the first mark portion overlaps with a first virtual line passing through a center of a right patella in a length direction of the right lower limb when viewed from the front of the user, an upper end of the first electrode portion and an upper end of the second electrode portion are positioned 10 mm below a lower end of the right patella, an end portion of the first electrode portion positioned closer to the second mark portion overlaps with the first virtual line, and an end portion of the second electrode portion positioned closer to the first mark portion is positioned 30 mm away from an end portion of the first electrode portion positioned closer to the second mark portion toward an inner side of the right lower limb, and in a second wrapped state obtained by wrapping the band-like member below a left knee such that the second mark portion overlaps with a second virtual line passing through a center of a left patella in a length direction of the left lower limb when viewed from the front of the user, the upper end of the first electrode portion and the upper end of the second electrode portion are positioned 10 mm below a lower end of the left patella, an end portion of the second electrode portion positioned closer to the first mark portion overlaps with the second virtual line, and the end portion of the first electrode portion positioned closer to the second mark portion is positioned 30 mm away from the end portion of the second electrode portion positioned closer to the first mark portion toward an inner side of the left lower limb.

11. The electrical treatment device according to claim 1, wherein the first mark portion is further configured to be aligned with the specific position of the right lower limb such that first electrode portion comes into contact with a first dermatome corresponding to the first target position, and the second electrode portion comes into contact with a second dermatome corresponding to the second target position; and the second mark portion is further configured to be aligned with the specific position of the left lower limb such that the second electrode portion comes into contact with the first dermatome corresponding to the fourth target position, and the first electrode portion comes into contact with the second dermatome corresponding to the third target position.

\* \* \* \* \*